United States Patent
Avramoff et al.

(10) Patent No.: US 11,559,541 B2
(45) Date of Patent: Jan. 24, 2023

(54) TOPICAL CAPECITABINE FOR THE TREATMENT OF HYPERPROLIFERATIVE SKIN CONDITIONS

(71) Applicant: TARO PHARMACEUTICAL INDUSTRIES LTD., Haifa Bay (IL)

(72) Inventors: Avi Avramoff, Haifa Bay (IL); Helena Shifrin, Haifa Bay (IL); Ron Schlinger, Haifa Bay (IL); Tzviel Sheskin, Haifa Bay (IL); Zeev Elkoshi, Haifa Bay (IL)

(73) Assignee: TARO PHARMACEUTICAL INDUSTRIES LTD., Haifa Bay (IL)

( * ) Notice: Subject to any disclaimer, the term of this patent is extended or adjusted under 35 U.S.C. 154(b) by 14 days.

(21) Appl. No.: 16/961,214

(22) PCT Filed: Jan. 18, 2019

(86) PCT No.: PCT/US2019/014334
§ 371 (c)(1),
(2) Date: Jul. 9, 2020

(87) PCT Pub. No.: WO2019/144032
PCT Pub. Date: Jul. 25, 2019

(65) Prior Publication Data
US 2021/0052620 A1 Feb. 25, 2021

Related U.S. Application Data

(60) Provisional application No. 62/618,981, filed on Jan. 18, 2018.

(51) Int. Cl.
| | |
|---|---|
| A61K 31/7068 | (2006.01) |
| A61P 17/12 | (2006.01) |
| A61K 9/00 | (2006.01) |
| A61K 31/122 | (2006.01) |
| A61K 31/196 | (2006.01) |
| A61K 31/437 | (2006.01) |
| A61K 31/4412 | (2006.01) |
| A61K 31/513 | (2006.01) |

(52) U.S. Cl.
CPC ........ *A61K 31/7068* (2013.01); *A61K 9/0014* (2013.01); *A61K 31/122* (2013.01); *A61K 31/196* (2013.01); *A61K 31/437* (2013.01); *A61K 31/4412* (2013.01); *A61K 31/513* (2013.01); *A61P 17/12* (2018.01)

(58) Field of Classification Search
CPC .............. A61K 31/7068; A61K 9/0014; A61K 31/122; A61K 31/196; A61K 31/437; A61K 31/4412; A61K 31/513; A61P 17/12
USPC .......................................................... 514/50
See application file for complete search history.

(56) References Cited

U.S. PATENT DOCUMENTS

| | | | |
|---|---|---|---|
| 5,610,160 A | 3/1997 | Sloan et al. | |
| 2015/0313901 A1* | 11/2015 | Ford | A61P 17/04 514/274 |
| 2019/0134063 A1* | 5/2019 | Glazer | A61K 31/195 |

FOREIGN PATENT DOCUMENTS

| | | |
|---|---|---|
| WO | 2006/081985 A1 | 8/2006 |
| WO | 2007/143212 A1 | 12/2007 |

OTHER PUBLICATIONS

Glossary of medical education terms, Institute of International Medical Education. http://www.iime.org/glossary.htm Accessed in Mar. 2013. (Year: 2013).*
Chang A.L.S. Recent Advances in Skin Cancer Treatment in Older Adults. A.L.S. Chang (ed.), Advances in Geriatric Dermatology, DOI 10.1007/978-3-319-18380-0_9, pp. 97-103, 2015. (Year: 2015).*
Jewell et al. Hydrolysis of a series of parabens by skin microsomes and cytosol from human and minipigs and in whole skin in short-term culture. Toxicology and Applied Pharmacology 225 (2007) 221-228. (Year: 2007).*
International Search Report dated Apr. 11, 2019 in corresponding International Patent Application No. PCT/US2019/014334.
Yen-Revollo, Jane L. et al., "Can Inhibiting Dihydropyrimidine Dehydrogenase Limit Hand-Foot Syndrome Caused by Fluoropyrimidines?", Clinical Cancer Research, Jan. 1, 2008, vol. 14, pp. 8-13.

* cited by examiner

*Primary Examiner* — Yih-Horng Shiao
(74) *Attorney, Agent, or Firm* — Medler Ferro Woodhouse & Mills PLLC

(57) ABSTRACT

The present invention relates to a novel and unexpected method of using topical Capecitabine composition to obtain therapeutically effective amounts of fluorouracil (FU) within the skin of a subject afflicted with hyperproliferative or inflammatory skin condition. The method comprising topically administering a pharmaceutical composition comprising Capecitabine or a hydrate or solvate thereof to the affected area of the skin of the subject, to form therapeutically effective amounts of FU within the skin.

13 Claims, 1 Drawing Sheet

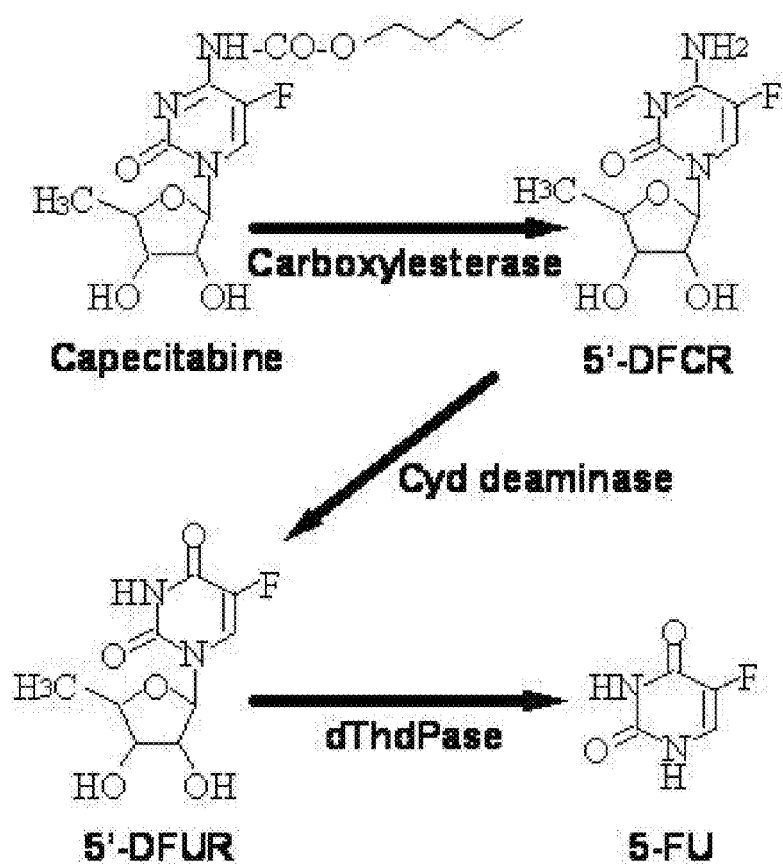

TOPICAL CAPECITABINE FOR THE TREATMENT OF HYPERPROLIFERATIVE SKIN CONDITIONS

BACKGROUND OF THE INVENTION

Maintenance of homeostasis in the skin requires a delicate balance among proliferation, differentiation, and apoptosis. Many common diseases of the skin, e.g., epidermis, such as actinic keratosis, psoriasis, squamous cell carcinoma, keratoacanthoma, and warts, are characterized by localized abnormal cell proliferation and growth.

Actinic keratosis (AK), also referred to as solar keratosis, is a skin disorder in which hyperplastic epidermal lesions develop in response to excessive and chronic exposure to ultraviolet (UV) radiation, such as sunlight. AK incidence is rising worldwide as a result of the progressive aging of populations and an increase in lifetime cumulative exposure to UV radiation. It has become a significant health care issue and is one of the most common reasons for consulting a dermatologist.

AK cutaneous lesions are pre-cancerous, as the majority of squamous cell carcinomas (SCCs) progress from preexisting AK and untreated lesions have up to a 20% risk of progression to squamous cell carcinoma. Furthermore, they are also accounted as a risk factor for melanoma and nonmelanoma skin cancer (NMSC). However, it is still not possible to predict which AK lesions will develop into SCC. Therefore, the lesions require careful evaluation and effective early treatment.

Basal cell carcinoma (BCC) is the most common malignant neoplasm found in human populations and constitutes roughly 80% of all non-melanoma skin cancers. BCC tumors have a characteristic slow progression and metastasis is extremely rare. Nonetheless, it can be very destructive and disfiguring since the invasive growth pattern can destroy cartilage and bone and reach vital structures (major vessels or CNS) with a fatal course. Thus early recognition is especially important.

Current treatments for AK and BCC include a variety of surgical and non-surgical therapies. Surgical therapies include chemical peeling, dermabrasion, curettage and electrosurgery, cryosurgery and laser surgery. Photodynamic therapy with photosensitizing agents such as, aminolevulinic acid hydrochloride (ALA) or hematoporphyrin is also available. These treatments can lead to unnecessary adverse effects in the surrounding tissue such as scar formation or other cosmetically disfiguring events.

In addition to the surgical therapies for AK and BCC, there are several FDA-approved drugs for treatment of AK and BCC. Obviously, the use of a drug in a topical manner to treat a skin disease state is desirable in that only a locally effective concentration of the drug needs to be attained in the skin. This is of great importance with systemic anti-cancer treatments which necessarily result in exposure of susceptible healthy cells, in non-target parts of the body, to cytotoxic chemicals and also have lower patient acceptance.

Topical FDA-approved drugs for AK and BCC are currently in the market, such as fluorouracil (e.g., 5-fluorouracil), Imiquimod and Ingenol mebutate.

Fluorouracil (FU), e.g., 5-fluorouracil, delivered topically is widely used to treat actinic or solar keratoses as well as superficial basal cell carcinomas. It is a fluorinated nucleoside known to be useful as an antineoplastic antimetabolite, affecting both DNA and RNA and leading to cell death.

Topical fluorouracil exists in solution formulations containing 2%, and 5% by weight fluorouracil, and cream formulations containing 1%, 4% and 5% by weight fluorouracil. However, these formulations, while beneficial, are irritating to the skin, causing side effects such as burning, allergic contact dermatitis, erythema, pain, pruritus, and ulceration. A cream formulation of 0.5% FU in which a part of the fluorouracil is incorporated into porous microspheres was approved by the FDA under the brand name Carac™. Although found to be less irritating than the previous formulations, irritation at the application site was reported in more than 90% of the patients who participated in the phase III clinical trials reported to the FDA, including symptoms of erythema, redness, dryness, burning, pain, erosion (loss of the upper layer of skin), and swelling.

The local skin reactions after the application of FU, imiquimod or ingenol mebutate, may be of such intensity that patients may require rest periods from treatment, or prematurely discontinue treatment before full clearance is achieved. Thus, there is still need for less irritating topical treatments for AK and BCC.

Furthermore, many of the current treatments for AK and BCC, although somewhat effective, can severely damage adjacent, healthy skin due to the fact that, in part, it is very difficult to differentiate between diseased and healthy skin tissue. As such, it is possible to either miss an affected, pre-cancerous area as well as to harm healthy skin, adjacent to the lesion.

Another drawback regarding the current topical medications for AK and BCC is their handling during preparation and application. Efudex™ instructions for example include that it should be applied with a nonmetal applicator or suitable glove, and if applied with fingers, the hands should be washed immediately. Carac™ instruction to the patient is to avoid contact with the eyes, eyelids, nostrils, and mouth and to wash hands immediately after applying the cream.

The barrier to absorption of topically applied drugs is the stratum corneum which comprises a dead, dry (5-10% $H_2O$), compact keratin-containing material. Moreover, AK is associated with tough, hardened areas of skin, therefore necessitate the penetration of the active ingredients through the stratum corneum in order to effectively treat the skin lesions.

U.S. Pat. No. 5,610,160 discloses a methylcarbonyl prodrug of FU for topical application having enhanced permeability across the external skin layer compared to FU. The FU prodrug is converted to FU by non-specific hydrolysis after the delivery to the skin. However, the conversion into FU is not specific to cancerous cells only.

There remains therefore, a need for a topical treatment for hyperproliferative skin conditions that will effectively and specifically target the pre-cancerous or cancerous skin cells while ensuring that adjacent healthy skin tissue is preserved, thus reducing skin irritation and damage to normal skin cells, improving patient compliance and increasing treatment success.

BRIEF SUMMARY OF THE INVENTION

The present disclosure is directed to a method of treating a hyperproliferative skin condition or inflammatory skin condition in a subject in need thereof, the method comprising topically administering a pharmaceutical composition comprising an effective amount of a therapeutic agent selected from Capecitabine, 5'-deoxy-5-fluorocytidine (5'DFCR), 5'-deoxy-5-fluorouridine (5'DFUR), or combinations thereof to the affected area of the skin of the subject, thereby treating the condition.

In some embodiments, the topical administration of the pharmaceutical composition comprising an effective amount of the therapeutic agent forms a therapeutically effective amounts of fluorouracil (FU) within the skin of the subject to treat the hyperproliferative or inflammatory skin condition.

In some embodiments, the therapeutic agent is Capecitabine. In some embodiments, the therapeutic agent is 5'-deoxy-5-fluorocytidine (5'DFCR). In some embodiments, the therapeutic agent is 5'-deoxy-5-fluorouridine (5'DFUR).

In some embodiments, the hyperproliferative skin condition is a pre-cancerous or cancerous skin condition. In some embodiments, the pre-cancerous skin condition is actinic keratosis. In some embodiments, the cancerous skin condition is selected from basal cell carcinoma, squamous cell carcinoma and melanoma.

In some embodiments, the hyperproliferative skin conditions can be non-cancerous inflammatory skin conditions, such as psoriasis, seborrhea and ichthyosis.

In some embodiments, the effective amount of therapeutic agent in the composition is from about 0.1% to about 15% by weight of the composition. In some embodiments, the effective amount of Capecitabine in the composition is from about 0.1% to about 15% by weight of the composition. In some embodiments, the effective amount of Capecitabine in the composition is from about 1% to about 10% by weight of the composition.

In some embodiments, the method further comprising topically administering at least one additional pharmaceutical agent useful for treating a hyperproliferative or inflammatory skin condition. In some embodiments, the therapeutic agent and the at least one additional pharmaceutical agent are in the same pharmaceutical composition. In some embodiments, the at least one additional pharmaceutical agent is selected from diclofenac, imiquimod, ingenol mebutate or other ingenol derivatives, uracil, 5-chloro-2,4-dihydroxypyridine (CDHP), eniluracil, photosensitizing agents, retinoids, interferons, α-hydroxy acids, and caustic agents.

In some embodiments, the topical administration is performed with an additional therapeutic treatment known to be effective in a hyperproliferative skin condition or an inflammatory skin condition. In some embodiments, the additional therapeutic treatment is selected from cryosurgery, curettage and dessication, excision, chemical peeling, dermabrasion, laser surgery and photodynamic therapy.

In some embodiments, the disclosure is directed to a topical pharmaceutical composition comprising an effective amount of a therapeutic agent selected from Capecitabine, 5'-deoxy-5-fluorocytidine (5'DFCR), 5'-deoxy-5-fluorouridine (5'DFUR), or combinations thereof in a pharmaceutically acceptable carrier, wherein the composition is suitable for topical administration and forms a therapeutically effective amounts of FU within the skin.

In some embodiments, the therapeutic agent in the composition is Capecitabine. In some embodiments, therapeutic agent in the composition is 5'-deoxy-5-fluorocytidine (5'DFCR). In some embodiments, the therapeutic agent in the composition is 5'-deoxy-5-fluorouridine (5'DFUR).

In some embodiments, the composition is a solid topical dosage form, a semisolid topical dosage form or a liquid topical dosage form. In some embodiments, the dosage form is in the form of dusting powder, paste, solution, ointment, cream, lotion, gel, spray, liniment or foam.

In some embodiments, the pharmaceutically acceptable carrier is one or more of a gelling agent, a solvent, a viscosifier, a penetration enhancer, a preservative, a thickening agent, an antioxidant, a chelating agent, an active ingredient stabilizer, an active ingredient solubilizer and/or a cosmetic ingredient.

In some embodiments, the composition comprises from about 1% to about 10% of the therapeutic agent by weight. In some embodiments, the composition comprises from about 0.1% to about 15% by weight Capecitabine. In some embodiments, the composition comprises from about 1% to about 10% Capecitabine by weight.

In some embodiments, the composition is suitable for application to a subject having a pre-cancerous or cancerous hyperproliferative skin condition. In some embodiments, the pre-cancerous skin condition is actinic keratosis. In some embodiments, cancerous skin condition is basal cell carcinoma.

In some embodiments, the composition further comprises at least one additional pharmaceutical agent useful for treating hyperproliferative skin conditions. In some embodiments, the at least one additional pharmaceutical agent is selected from diclofenac, imiquimod, ingenol mebutate or other ingenol derivatives, uracil, 5-chloro-2,4-dihydroxypyridine (CDHP), eniluracil, photosensitizing agents, retinoids, interferons, α-hydroxy acids, and caustic agents.

In some embodiments, the composition is used in conjunction with at least one therapeutic treatment known to be effective in hyperproliferative or inflammatory skin conditions. In some embodiments, the therapeutic treatment is selected from cryosurgery, curettage and dessication, excision, chemical peeling, dermabrasion, laser surgery and photodynamic therapy.

In some embodiments, the disclosure is directed to a method of providing fluorouracil (FU) to a subject in need thereof, the method comprising topically administering a pharmaceutical composition comprising an effective amount of a therapeutic agent selected from Capecitabine, 5'-deoxy-5-fluorocytidine (5'DFCR), 5'-deoxy-5-fluorouridine (5'DFUR), or combinations thereof to the skin of the subject, whereby the therapeutic agent is converted to FU in the skin.

In some embodiments, the disclosure is directed to a method of reducing adverse effects to fluorouracil (FU) in a subject with a hyperproliferative skin condition or inflammatory skin condition, the method comprising topically administering a pharmaceutical composition comprising an effective amount of a therapeutic agent selected from Capecitabine, 5'-deoxy-5-fluorocytidine (5'DFCR), 5'-deoxy-5-fluorouridine (5'DFUR), or combinations thereof to the skin of the subject, whereby the therapeutic agent is converted to FU in hyperproliferating skin cells at a greater rate than non-hyperproliferating skin cells, thereby reducing adverse effects.

In some embodiments, the disclosure is directed to a method of decreasing adverse effects of administration of fluorouracil (FU), the method comprising topically administering a pharmaceutical composition comprising an effective amount of a therapeutic agent selected from Capecitabine, 5'-deoxy-5-fluorocytidine (5'DFCR), 5'-deoxy-5-fluorouridine (5'DFUR), or combinations thereof to the skin of the subject, whereby the therapeutic agent is converted to FU in the skin after administration, whereby adverse effects are decreased by a reduction of exposure to FU during administration.

In some embodiments, the disclosure is a method of reducing unintended exposure to fluorouracil (FU) during administration of FU to a subject, the method comprising topically administering a pharmaceutical composition comprising an effective amount of a therapeutic agent selected from Capecitabine, 5'-deoxy-5-fluorocytidine (5'DFCR), 5'-deoxy-5-fluorouridine (5'DFUR), or combinations thereof to the skin of the subject, whereby the therapeutic agent is converted to FU in the skin, whereby unintended exposure does not occur during the administration process.

BRIEF DESCRIPTION OF THE FIGURES

FIG. 1 is a schematic representation of the enzymatic degradation pathway of Capecitabine to 5-fluorouracil.

DETAILED DESCRIPTION OF THE INVENTION

The present invention relates to a novel and unexpected use of Capecitabine, a FU prodrug, in the treatment of hyperproliferative skin conditions following topical application. Capecitabine is an FDA-approved oral drug under the Trade name of Xeloda™ used for the treatment of metastatic colorectal cancer, metastatic breast cancer and adjuvant colon cancer. When taken orally, the Capecitabine pro-drug is metabolized to FU via a three-step enzymatic process, in which the third step is localized predominantly in the tumor tissue.

The present invention relates to a novel and unexpected method of using topical Capecitabine composition to obtain therapeutically effective amounts of fluorouracil (FU) within the skin of a subject afflicted with hyperproliferative or inflammatory skin condition, the method comprising topically administering a pharmaceutical composition comprising an effective amount of Capecitabine or a hydrate or solvate thereof to the affected area of the skin of the subject, to form therapeutically effective amounts of FU within the skin.

Unexpectedly, the inventors of the present invention have discovered that FU can be formed in therapeutically effective amounts in the skin following topical administration of the pro-drug Capecitabine (and its enzymatically metabolized forms) specifically in hyperproliferating skin tissue such as actinic keratosis skin. Surprisingly, topical administration of Capecitabine allows the conversion of Capecitabine to FU in hyperproliferating skin, while very low FU was formed in healthy skin. Thus, the inventors of the present invention have discovered that topical Capecitabine is effective in the treatment of hyperproliferative skin conditions, including pre-cancerous and cancerous skin conditions. The in situ formation of FU specifically in hyperproliferating skin is highly advantageous since it might reduce the damage of FU to normal skin cells in the surrounding healthy tissue and decrease the irritation and local skin reactions following topical administration.

The use of topical Capecitabine compositions of the present invention would improve patient safety during handling and patient compliance, prevents prematurely discontinuation of treatment and hence increases treatment success over that of the standard FU treatment. In some embodiments, the use of topical Capecitabine can prolong the treatment duration by preventing premature discontinuation of treatment. Moreover, Capecitabine is metabolized into FU through a specific cascade of enzymatic processes, enabling selective FU exposure predominantly in pre-cancerous and cancerous cells. This cascade of enzymatic processes is outlined in FIG. 1. Generally speaking, Capecitabine is converted to 5'-deoxy-5-fluorocytidine (5'DFCR) by carboxylesterase (CES). 5'DFCR is then converted to 5'-deoxy-5-fluorouridine (5'DFUR) by cytidine deaminase. 5'DFUR is converted to 5-fluorouracil by thymidine phosphorylase (TP). This enzymatic degradation allows administration of one or more FU-precursors to effect a targeted delivery of a pharmacologically effective amount of FU specifically into pre-cancerous and cancerous cells.

Drug penetration through the stratum corneum is an obstacle in the development of any topical treatment. Moreover, AK is associated with tough, hardened areas of skin, therefore necessitate the penetration of the active ingredients into the epidermis skin layer. Being a more lipophilic compound than FU, Capecitabine exhibits better skin penetration than FU, leading to higher levels of the drug in the skin.

Another advantage of using the Capecitabine prodrug and not FU for topical treatment is its lower toxicity during handling. Being less hazardous, the topical use of Capecitabine may increase the safety during handling and patient compliance, and also may reduce the precautions needed during the manufacturing process.

In one embodiment, the present invention relates to the use of topical Capecitabine compositions for the treatment of hyperproliferative skin conditions.

In another embodiment, the present invention relates to the use of topical Capecitabine compositions for the treatment of inflammatory skin conditions. In one embodiment, the inflammatory skin conditions are selected from acne, rosacea, atopic dermatitis, Vitiligo and Alopecia areata.

According to a preferred embodiment of the present invention, the hyperproliferative skin conditions include pre-cancerous or cancerous skin conditions.

In one embodiment, the hyperproliferative skin conditions are pre-cancerous skin conditions, such as but not limited to actinic keratoses.

In an additional embodiment, the hyperproliferative skin conditions are cancerous skin conditions, such as but not limited to basal cell carcinoma, squamous cell carcinoma and melanoma.

In yet another embodiment, the hyperproliferative skin conditions can be non-cancerous skin conditions, such as psoriasis, seborrhea and ichthyosis.

Accordingly, the present invention provides a pharmaceutical composition in a dosage form suitable for topical administration to a human in need thereof, comprising a pharmacologically effective amount of Capecitabine in a pharmaceutically accepted carrier.

In one embodiment, the topical Capecitabine composition comprises from about 0.1% to about 15% by weight Capecitabine in a pharmaceutically accepted carrier, more preferably the topical Capecitabine composition comprises from about 1% to about 10% Capecitabine.

In one embodiment, the topical Capecitabine composition is in the form of solution, ointment, cream, lotion, gel, spray or foam.

In another embodiment, the present invention provides a method of treating hyperproliferative or inflammatory skin conditions, in a subject in need thereof, the method comprising topically administering a therapeutically effective amount of a pharmaceutical composition of Capecitabine to the affected area of the skin.

In one embodiment, the pre-cancerous or cancerous skin condition is actinic keratosis, basal cell carcinoma, squamous cell carcinoma or melanoma.

In yet another embodiment, the hyperproliferative skin conditions can be non-cancerous skin conditions, such as psoriasis, seborrhea and ichthyosis.

In one embodiment, the inflammatory skin conditions are selected from acne, rosacea, atopic dermatitis, Vitiligo and Alopecia areata.

In a preferred embodiment, the pre-cancerous skin condition is actinic keratosis and the cancerous skin condition is basal cell carcinoma.

Another aspect of the present invention is a combination of Capecitabine topical treatment with other therapeutic treatments effective for hyperproliferative skin conditions.

In one embodiment, the present invention provides a method of treating a hyperproliferative or inflammatory skin condition, selected from pre-cancerous, cancerous skin condition and inflammatory skin condition, in a subject in need thereof, the method comprising topically applying a pharmaceutical composition comprising an effective amount of Capecitabine or a hydrate or solvate thereof to the affected area of the skin of the subject.

In another embodiment, the present invention provides a topical pharmaceutical topical composition comprising an effective amount of Capecitabine or a hydrate or solvate thereof in a pharmaceutically accepted carrier, wherein the composition is topically applied on the skin of a subject afflicted with hyperproliferative or inflammatory skin condition, to form therapeutically effective amounts of FU within the skin.

In one embodiment, the present invention relates to a method of using topical Capecitabine composition to obtain therapeutically effective amounts of fluorouracil (FU) within the skin of a subject afflicted with hyperproliferative or inflammatory skin condition, the method comprising topically administering a pharmaceutical composition comprising an effective amount of Capecitabine or a hydrate or solvate thereof to the affected area of the skin of the subject, to form therapeutically effective amounts of FU within the skin.

In another embodiment, the present invention relates to Capecitabine topical compositions and to a method of treating a hyperproliferative or inflammatory skin condition in a subject in need thereof, comprising topically applying a pharmaceutical composition comprising an effective amount of Capecitabine to the affected area of the skin of the subject.

According to one embodiment of the invention, the hyperproliferative skin conditions are pre-cancerous or cancerous skin conditions.

According to yet another embodiment, the hyperproliferative skin conditions can be non-cancerous skin conditions.

According to specific embodiments, the hyperproliferative skin conditions to be treated according to the principles of the present invention, include, but are not limited to, actinic keratoses, psoriasis, common warts, genital warts, keratoacanthoma, seborrhoic keratosis, seborrhea, ichthyosis, basal cell carcinoma, squamous cell carcinoma and melanoma. Each possibility represents a separate embodiment of the invention.

In one embodiment, the hyperproliferative skin conditions are pre-cancerous skin conditions, such as but not limited to actinic keratoses.

In particular embodiments, actinic keratoses conditions are selected from the group consisting of actinic keratosis (also called solar keratosis), hypertrophic actinic keratosis, Bowenoid actinic keratosis, arsenical keratosis, hydrocarbon keratosis, thermal keratosis, radiation keratosis, chronic scar keratosis, viral keratosis, actinic cheilitis, Bowen's disease, erythroplaquia of queyrat, oral erythroplaquia, leukoplakia and intraepidermal epithelialoma.

In an additional embodiment, the hyperproliferative skin conditions are cancerous skin conditions, such as but not limited to basal cell carcinoma, squamous cell carcinoma and melanoma.

In a preferred embodiment, the pre-cancerous skin condition is actinic keratosis and the cancerous skin condition is basal cell carcinoma.

The inventors of the present invention have surprisingly discovered that the prodrug capecitabine is effectively converted into FU in skin cells, predominantly in hyperproliferating skin cells, more specifically in pre-cancerous and cancerous skin cells, and particularly in skin cells affected with AK and BCC.

According to various embodiments of the present invention, the percentage of Capecitabine that is converted to FU in the skin following topical application is at least 0.1%, at least 3%, at least 5%, at least 8%, at least 10%, at least 20%, at least 30%, at least 40%, at least 50%, at least 60%, at least 70%, at least 80% or at least 90% of the applied dose of Capecitabine.

In one embodiment, the present invention provides a pharmaceutical composition in a dosage form suitable for topical administration to a human in need thereof comprising a pharmacologically effective amount of Capecitabine in a pharmaceutically accepted carrier.

The precise amount of Capecitabine effective for treating the hyperproliferative skin conditions will vary according to factors known in the art including, but not limited to, the physical and chemical nature of the particular compound being administered; the extent of Capecitabine metabolism to FU; the physical and chemical nature of the formulation; the size, location, and histological type of the lesion; and the intended dosing regimen.

In one embodiment, the topical composition comprises from about 0.01% to about 15% by weight Capecitabine in a pharmaceutically accepted carrier.

In another embodiment of the invention, the topical Capecitabine composition comprises from about 0.1% to about 10% Capecitabine by weight.

In a preferred embodiment, the topical composition comprises from about 1% to about 10% Capecitabine by weight.

According to one embodiment, the Capecitabine can be present in the composition as a hydrate or solvate thereof.

Pharmaceutical compositions include any formulations which are pharmaceutically acceptable for topical delivery of the compounds of the invention. The choice of topical formulation will depend on several factors, including the physiochemical characteristics of the particular compound(s) of the invention and of other excipients present, their stability in the formulation, available manufacturing equipment, and cost constraints.

The Capecitabine compositions of the present invention can be in any suitable carrier known in the art and is pharmaceutically acceptable for topical delivery including, but not limited to, solution, ointment, cream, lotion, gel, spray or foam.

In some embodiments, the pharmaceutically acceptable carrier is one or more of a water in oil emulsion, an adsorbing agent, an emulsifying agent, a solvent (e.g., liquid or semi-solid solvent), a stabilizer, a permeation enhancer, a lipophilic material, e.g., an oil, an emollient, a hydrocolloidal agent, or a gelling agent. Suitable pharmaceutically acceptable carrier suitable for topical administration are known in the art, e.g., Garg et al., Comprehensive review on additives of topical dosage forms for drug delivery," Drug Deliv, 22(8):969-987 (2015).

In a preferred embodiment, the compositions of the present invention are in the form of a hydroalcoholic gel, a cream or an ointment.

Preparation of suitable formulations is within the skill of those in the art, and suitable excipients for inclusion in any such formulation include, for example, gelling agents, solvents, viscosifiers, penetration enhancers, preservatives, thickening agents, antioxidants, chelating agents, and cosmetic ingredients, such as fragrances and colourings.

Suitable solubilizing agents include, but are not limited to, ethanol, isopropanol, benzyl alcohol, cetyl alcohol, dimthylsulfoxide (DMSO), polyethylene glycols (PEGs), propylene glycol, hexylene glycol, glycerol and diethylene glycol monoethyl ether. In some embodiments, the solvents may include oils and waxes such as paraffins, mineral oil, coconut oil, castor oil, and medium chain triglycerides. In other embodiments, the solubilizing agents include cyclodextrins, such as β-cyclodextrin (BCD) or hydroxypropyl-β-cyclodextrin (HPBCD). The solubilizing agents can be included as a single solvent or a combination of more than one solubilizing agent.

Suitable gelling agents include, but are not limited to, water soluble cellulose derived polymers, such as hydroxyalkyl cellulose polymers (e.g. hydroxymethylcellulose, hydroxyethylcellulose, hydroxypropylcellulose and hydroxypropylmethylcellulose), carboxymethyl cellulose, methylhydroxyethyl cellulose and methyl cellulose, carbomers (e.g. carbopol); xanthan and carrageenans. The gelling agent may be added in any suitable amount, such as between about 1 to about 5% (w/w). In one embodiment, the gelling agents are carbomers, including, but are not limited to, carbomer 910, 934P (Carbopol® 934P), 940, 941, 974P (Carbopol® 974P), 980 (Carbopol® 980) and 981.

Suitable emulsifiers for use in the compositions of the present invention include, but are not limited to, *glycine soja* protein, sodium lauroyl lactylate, polyglyceryl-4 diisostearate-polyhydroxystearate-sebacate, behentrimonium methosulfate-cetearyl alcohol, non-ionic emulsifiers like emulsifying wax, polyoxyethylene oleyl ether, PEG-40 stearate, carbomer, polysorbates and sorbitan esters, cetostearyl alcohol (cetearyl alcohol), ceteareth-12, ceteareth-20, ceteareth-25, ceteareth-30, ceteareth alcohol, Ceteth-20, oleic acid, oleyl alcohol, glyceryl stearate, PEG-75 stearate, PEG-100 stearate, and PEG-100 stearate, ceramide 2, ceramide 3, stearic acid, cholesterol, laureth-12, steareth-2, and steareth-20, or combinations/mixtures thereof, as well as cationic emulsifiers like stearamidopropyl dimethylamine and behentrimonium methosulfate, or combinations/mixtures thereof.

Suitable penetration enhancers include, but are not limited to, polyols and esters, including polyethylene glycol, polyethylene glycol monolaurate, and butanediol; sulfoxides, including dimethylsulfoxide (DMSO) and decylmethylsulfoxide; ethers, including diethylene glycol monoethyl ether (e.g., Transcutol. P) and diethylene glycol monomethyl ether; fatty acids, including lauric acid, oleic acid, and valeric acid; fatty acid esters, including isopropyl myristate, isopropyl palmitate, methyl propionate, and ethyl oleate; nitrogenous compounds including urea, dimethyl acetamide, dimethylformamide 2-pyrrolidone, ethanolamine, methyl-2-pyrrolidone, diethanolamine, and triethanolamine; terpenes; alkanones; organic acids, including salicylic acid, citric acid, and succinic acid; and any mixtures thereof.

Suitable thickening agents include polyqueternium-10, Sepino™ P600, PEG 120 methyl glucose dioleate, sodium alginate, gum arabic, cellulose derivatives, such as methylcellulose, hydroxymethylcellulose, hydroxyethylcellulose, hydroxylpropylcellulose or hydroxypropylmethylcellulose, guar gum or its derivatives, xanthan gum, or combinations thereof.

Suitable preservatives will be apparent to those skilled in the art, and include the parabens, such as methylparaben, propylparaben, isopropylparaben, butylparaben, and isobutylparaben, and their salts such as sodium butylparaben, benzoic acid and its salts and esters, benzyl alcohol, urea derivatives such as diazolidinyl urea, imidazolidinyl urea, and DMDM hydantoin, sorbic acid and its salts, and the like. Preservatives employed solely for that purpose will generally form 1% (w/w) or less of the final topical formulation. Preferably, the preservatives are a combination of parabens, such as methylparaben and propylparaben.

Examples of water-soluble antioxidants include ascorbic acid and its salts, such as sodium ascorbate, isoascorbic acid and its salts, sodium sulfite, sodium metabisulfite, sodium thiosulfite, thiols such as thioglycerol, thiosorbitol, thiourea, thioglycolic acid, and cysteine, and the like. Examples of oil-soluble antioxidants include BHT (butylated hydroxytoluene), BHA (butylated hydroxyanisole), tocopherol (vitamin E), tocopheryl acetate, ascorbyl palmitate, hydroquinone, di-t-butylhydroquinone, propyl gallate, and the like. Preferably, the antioxidant is BHT.

Optional chelating agents include, but are not limited to, EDTA (ethylenediaminetetraacetic acid) and its salts, for example disodium EDTA, trisodium NTA, etidronic acid and its salts, sodium dihydroxyethylglycinate, citric acid and its salts, and the like. Preferably, the chelating agent is EDTA or its salts.

Suitable colorants and fragrances will be a matter of choice, provided only that they should be compatible with the formulation.

Some of the excipient substances described above can have more than one function in a formulation. For example, a substance can be both a solvent and a penetration enhancer, or both an emollient and a penetration enhancer. The categorizations of materials described above are not to be construed as limiting or restricting in any manner.

In some embodiments, the present invention further relates to Capecitabine topical compositions wherein, the compositions are stable for a period of at least 6 months at accelerated storage conditions. In some embodiments, the compositions are stable for a period of at least 12 months at room temperature conditions.

In some embodiments, the term "stable" as used herein refers to physical stability and/or chemical stability of the active agent in a topical composition, wherein changes in the drug assay values and/or impurities content are less than about 5%, during stability study of the composition at 25° C. and 60% relative humidity (referred as "RT conditions"), or 40° C. and 75% relative humidity (referred as "accelerated storage conditions"), for durations such as 1, 3, 6, 12, 18, or 24 months.

The topical Capecitabine compositions of the present invention exhibit effective skin penetration to the affected skin area. According to some embodiments of the present invention, at least 0.01%, at least 0.1%, at least 0.5%, at least 1%, at least 2%, at least 3%, at least 4%, at least 5%, at least 6%, at least 7%, at least 8%, at least 9% or at least 10% of the applied Capecitabine dose penetrates into the skin. In one embodiment, at least 0.5%, at least 1%, at least 2%, at least 3%, at least 4%, at least 5%, at least 6%, at least 7%, at least 8%, at least 9% or at least 10% of the applied Capecitabine dose penetrates into the epidermis skin layer.

According to additional embodiments, about 0.5% to about 20% of the applied Capecitabine penetrates into the skin, more preferably, about 1% to about 10% of the applied Capecitabine penetrates into the skin. In one embodiment, about 0.5% to about 20% of the applied Capecitabine penetrates into the epidermis skin layer, more preferably, about 1% to about 10% of the applied Capecitabine penetrates into the epidermis skin layer.

According to yet additional embodiments, the amount of FU formed within the skin after the application of the Capecitabine composition, is from about 0.01% to about 90%, or about 0.01% to about 40%, of the applied Capecitabine dose, more preferably, from about 0.1% to about 20% of the applied Capecitabine dose, and more preferably, from about 0.1% to about 10% of the applied Capecitabine dose. In one embodiment, the amount of FU found within the epidermis is from about 0.01% to about 20% of the applied Capecitabine dose, more preferably, from about 0.1% to about 10% of the applied Capecitabine dose.

According to one embodiment, the amount of FU formed within the skin after the application of the Capecitabine composition, is from about 1 µg to about 100,000 µg per 1 $cm^2$ of skin tissue. In another embodiment, the amount of FU formed within the skin after the application of the Capecitabine composition, is from about 10 µg to about 10,000 µg per 1 $cm^2$ of skin tissue. In some embodiments, the amount of FU formed within the skin after the application of the Capecitabine composition, is from about 0.01 mg to about 100 mg per 1 $cm^2$ of skin tissue. In another embodiment, the amount of FU formed within the skin after the application of the Capecitabine composition, is from about 0.01 mg to about 10 mg per 1 $cm^2$ of skin tissue.

According to one aspect, the present invention provides a method of treating a pre-cancerous or cancerous skin condition in a subject in need thereof, the method comprising topically administering a therapeutically effective amount of a pharmaceutical composition of Capecitabine to the affected area of skin of the subject.

A "therapeutically effective amount" or "therapeutically effective amounts" means the amount that, when administered to a subject for treating a disease, is sufficient to effect treatment for that disease.

The term "treating" or "treatment" of a disease, as used herein, includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "hyperproliferative", as used herein, is used to describe a condition with abnormally high proliferation of skin cells, particularly abnormal proliferation of keratinocytes or melanocytes. This condition can be pre-cancerous or cancerous skin condition, as well as non-cancerous condition.

The term "cancerous", as used herein, is used to describe a condition affected by or showing abnormalities characteristic of cancer.

The term "pre-cancerous", as used herein, is used to describe a condition that may potentially (or is likely to) become cancer or is associated with an increased risk of cancer. This term can be replaced by the term premalignant.

The term "non-cancerous", as used herein, is used to describe a skin condition that is characterized by skin cell hyperproliferation, but cannot be considered as pre-cancerous or cancerous condition as described herein.

According to one embodiment of the invention, the pre-cancerous or cancerous skin condition is selected from actinic keratosis, basal cell carcinoma, squamous cell carcinoma, and melanoma.

According to a preferred embodiment, the pre-cancerous skin condition is actinic keratosis and the cancerous skin condition is basal cell carcinoma.

According to one embodiment, the inflammatory skin conditions are selected from acne, rosacea, atopic dermatitis, Vitiligo and Alopecia areata.

Another aspect of the present invention is a combination of Capecitabine topical treatment with additional therapeutic treatments known to be effective in hyperproliferative skin conditions.

According to one embodiment, the additional therapeutic treatment is a surgical procedure such as cryosurgery, curettage and dessication, excision, chemical peeling, dermabrasion, or laser surgery.

According to another embodiment, the additional therapeutic treatment is photodynamic therapy with photosensitizing agents such as, aminolevulinic acid hydrochloride (ALA) or hematoporphyrin.

According to another embodiment, Capecitabine topical treatment can be combined with any other additional pharmaceutical agent useful for treating hyperproliferative skin conditions such as AK or BCC.

In one embodiment, the additional pharmaceutical agents are selected from the group consisting of photosensitizing agents, retinoids, interferons, $\alpha$-hydroxy acids, and caustic agents. The photosensitizing agent can be, for example, 5-ALA, methoxsalen, porfimer, or verteporfin. The caustic agent can be, for example, trichloroacetic acid or phenol.

In an additional embodiment, the additional pharmaceutical agents are selected from diclofenac, imiquimod and ingenol mebutate or other ingenol derivatives. In yet additional embodiment, the additional pharmaceutical agents are dihydropyrimidine dehydrogenase (DPD) inhibitors, including uracil, 5-chloro-2,4-dihydroxypyridine (CDHP), or eniluracil.

Having now generally described this invention, the same will be better understood by reference to the following Examples, which are provided herein solely for purposes of illustration only and are not intended to be limiting of the invention or any embodiment thereof, unless so specified.

EXAMPLES

Example A

To evaluate the conversion of Capecitabine into FU in human skin, Capecitabine can be applied to human skin and the levels of Capecitabine and FU can be measured by analytical methods known in the art. Skin excised from healthy donors as well as from actinic keratosis patients can be used for these experiments. The skin can be freshly excised and maintained in physiological conditions to retain the enzymatic activity within the skin.

The penetration/permeation model is a well-validated tool for the study of percutaneous absorption of topically applied drugs. This model can be used herein to evaluate the conversion of the Capecitabine prodrug into the FU active drug within the skin by direct measurement of both Capecitabine and FU levels in the tissue. The model uses freshly excised human skin mounted in specially designed diffusion chambers that allow the skin to be maintained at a temperature and humidity that match real use conditions and the application of the drug.

To determine the degree of prodrug conversion into the active drug, both Capecitabine and FU can be recovered from each skin layer (stratum corneum, epidermis, and partial dermis) and the receiver compartment and their amounts in each skin layer can be determined.

Example 1: Topical Capecitabine Compositions

Formulation A: Hydroalcoholic gel

| Ingredient | Weight Percent |
|---|---|
| Capecitabine | 1.0-15.0 |
| Alcohol 96% USP | 10.0-40.0 |
| DMSO | 5.0-10.0 |
| BHT | 0.05-0.1 |
| Methylparaben | 0.1-0.3 |
| Propylparaben | 0.1-0.5 |
| Carbopol 934P | 0.5-2.0 |
| Purified Water | q.s |
| Hydroxypropyl-β-cyclodextrin (HP-b-Cyclodextrin) | 0.5-1.5 |
| Sepineo P600 | 0.5-4.0 |

Formulation B: Hydroalcoholic gel

| Ingredient | Weight Percent |
|---|---|
| Capecitabine | 1.0-15.0 |
| Alcohol 96% USP | 10.0-40.0 |
| DMSO | 5.0-10.0 |
| BHT | 0.05-0.1 |
| Methylparaben | 0.1-0.3 |
| Propylparaben | 0.1-0.5 |
| Carbopo 934P | 0.5-2.0 |
| Purified Water | q.s |
| Polyethylene Glycol 400 (PEG-400) | 0.5-7.0 |
| Sepineo P600 | 0.5-4.0 |

Formulation C: Oil in water (cream)

| Ingredient | Weight Percent |
|---|---|
| Capecitabine | 1.0-15.0 |
| Steareth-2 | 0.5-5.0 |
| Steareth-20 | 0.5-5.0 |
| Mineral oil | 5.0-30.0 |
| EDTA | 0.05-0.1 |
| Methylparaben | 0.1-0.3 |
| Propylparaben | 0.1-0.5 |
| Isopropyl myristate | 1.0-10.0 |
| Purified Water | q.s |
| Hydroxypropyl-β-cyclodextrin (HP-b-Cyclodextrin) | 0.5-2.0 |
| Polyethylene Glycol 400 (PEG-400) | 0.5-7.0 |

Formulation D: Ointment

| Ingredient | Weight Percent |
|---|---|
| Capecitabine | 1.0-15.0 |
| Super White Petrolatum | 60.0-80.0 |
| Paraffin NF | 1.0-10.0 |
| White wax NF | 1.0-10.0 |
| Mineral Oil USP | 1.0-10.0 |
| Propylene carbonate NF | 1.0-5.0 |
| Polyethylene Glycol 400 (PEG-400) | 0.5-10.0 |

Formulation E: hydroalcoholic gel

| Ingredient | Weight Percent |
|---|---|
| Capecitabine | 5.00 |
| Alcohol 96% USP | 24.00 |
| DMSO | 5.00 |
| Sepineo P600 | 3.00 |
| β-Cyclodextrin | 0.50 |
| Methylparaben | 0.00 |
| Propylparaben | 0.00 |
| Purified Water | 62.50 |

Example 2: Evaluation of In Situ Capecitabine Metabolism into FU in Viable Fresh Skin Samples Originated from Healthy and Actinic Keratosis (AK) Human Subjects The penetration/permeation ex vivo model is a well-validated tool for the study of percutaneous absorption of topically applied drugs. This model was utilized herein to evaluate the conversion of the Capecitabine prodrug into the FU active drug within the skin by direct measurement of both Capecitabine and FU levels in the tissue. The model uses freshly excised human skin mounted in specially designed diffusion chambers that allow the skin to be maintained at a temperature and humidity that match real use conditions and the application of the drug.

In Situ Capecitabine Metabolism into 5-FU in Healthy Skin:

Experimental Design:

Human skin from a healthy donor was mounted between the donor and receptor compartment of a vertical diffusion cell. The skin was dosed with 5% capecitabine formulation (formulation E) or placebo. A vertical diffusion cell was also prepared to which no formulation was applied to serve as a blank. Receptor solution was added to the receptor compartment in a fashion such that no air bubbles were present during testing. Receptor solution aliquots were collected at 1, 2, 4, 6, 8 and 24 h time points and analyzed using a single LC-MS/MS analytical method. Following the final time point collection, residual formulation was removed from the surface of the skin and then the skin surface was taped striped up to 5 times to remove residual formulation and the top of the skin surface layers (Stratum Corneum). The epidermis was then heat-separated from the dermis by placing the skin into an incubator at 60° C. for 2 min, followed by manually separation using gloved hands. The amount of each drug delivered to epidermis and dermis was then determined by LC-MS/MS.

Results:

Total Amount of Capecitabine and FU in the Skin and the Receptor Solution:

Extremely low levels of FU were detected in the skin of only one replicate tested and no FU was detected in the other replicates tested.

Specifically the levels of capecitabine and FU after 24 h, were measured to be 23,402 ng and 8.07 ng, respectively.

In Situ Capecitabine Metabolism into FU in AK Skin:

Experimental Design:

AK samples from human AK donor were obtained fresh. The LC-MS/MS analytical method, receptor solution, extraction fluid, and sampling time points used in the healthy skin were also used with the AK samples. The skin sample was mounted between the donor and receptor compartment of a vertical diffusion cell. AK skin was mounted onto micro Franz cell with adapter. Receptor solution (PBS+0.01% Brij)

was added to the receptor compartment of each cell. After about 0.5 h, the skin was dosed with 5% capecitabine formulation (formulation E) or placebo. Receptor solution aliquots were collected at 1, 2, 4, 6, 8 and 24 h time points and analyzed using a single LC-MS/MS analytical method. Following 24 h, the residual formulation was removed from the surface of the skin. It was not possible to separate the epidermis from the dermis of the AK sample (due to the limited size of the samples); therefore the whole tissue (epidermis+dermis) was added to homogeniser tubes. The amount of capecitabine and fluorouracil in the skin and receptor solution was determined by LC-MS/MS.

Results: Table 1 below summarizes the amounts (ng) of Capecitabine and FU measured within the AK skin (epidermis and dermis) and in the receptor solution following 24 hours. Two samples derived from the AK skin were analyzed in parallel. As revealed from the results, a significant conversion of FU in situ was observed in the AK skin (first sample exhibited 3.9% conversion out of total amount of Capecitabine permeating/penetrating and second exhibited 8.5% conversion out of total amount of Capecitabine permeating/penetrating). These results are unexpected in view of the data obtained in the healthy skin in which the level of FU detected within the skin and in the receptor solution was very low, if any.

TABLE 1

|  | Total Capecitabine in skin and receptor solution (ng) | Total FU in skin and receptor solution (ng) | % FU of Capecitabine measured |
|---|---|---|---|
| AK donor-sample 1 | 62,665 ng | 2,465 ng | 3.9% |
| AK donor-sample 2 | 31,586 ng | 2,696 ng | 8.5% |

Example 3: Stability of Capecitabine Topical Compositions

The chemical stability of Formulation E was evaluated following 2 weeks in 4° C. The levels of Capecitabine (the Assay results) and the levels of total impurities were determined during this stability period using HPLC technique. Table 2 below depicts the stability data obtained.

TABLE 2

| ASSAY (%) | 110.80% |
|---|---|
| FU | Not detected |
| RRT 0.47 |  |
| Related Compound A | 0.09 |
| Related Compound B | 0.26 |
| RRT 0.68 |  |
| RRT 1.02 |  |
| Related Compound C |  |
| Total (%) | 0.35 |

In some embodiments, the formulations samples can be kept in RT conditions (25° C.) for 24 months and in accelerated storage conditions (40° C.) for 6 months. The levels of Capecitabine (the Assay results) and the levels of total impurities can be determined during these stability periods using HPLC technique.

Example 4: Skin Penetration Studies

The penetration/permeation model is a well-validated tool for the study of percutaneous absorption of topically applied drugs. The model uses excised human skin mounted in specially designed diffusion chambers that allow the skin to be maintained at a temperature and humidity that match real use conditions. The composition is applied to the surface of the skin and the penetration of the compound is measured by monitoring its rate of appearance in the stratum corneum, epidermis and dermis skin layers, as well as the receptor solution flowing underneath the skin samples. Also, this in vitro system has the potential for carefully controlling many of the potential variables involved in topical application, like dosing volumes, humidity, temperature, drug stability, skin thickness, etc.

The dermatomed skin is positioned between the two halves of the diffusion cell with the stratum corneum facing the donor compartment allowing for drug application. The drug concentrations permeating across human skin and drug penetration within the different skin layers are measured.

To determine the penetration of Capecitabine into the skin from the various topical compositions (formulations A-E, as listed in Example 1), an in vitro penetration study is conducted using cadaver skin. The total amount of capecitabine within the skin and receptor cell, as well as the flux rate through the skin to the receptor cell, are analyzed.

In some embodiments, the Capecitabine compositions can be applied to freshly excised skin from healthy donors as well as from actinic keratosis patients, to allow the measurement of both Capecitabine and 5-FU. The total amounts of capecitabine and 5-FU within the skin and receptor cell can be measured. The 5-FU 5% cream formulation (Efudx™) can be used as a comparative control in order to verify that the skin levels of 5-FU, achieved from the application of the Capecitabine formulations, are comparable to the clinically approved drug.

Few donors of human skin are used for all tested formulations. The formulation samples are applied at an infinite dose under occlusion, for a 24-48 hour study. The receptor solution is sampled at specified time-points after application. The flux of the permeation through the skin is calculated for all tested formulations using the slope of the linear phase of the permeation study.

For the analysis of the skin penetration study, skin extracts are analyzed with HPLC-UV (HPL-150). The electrical resistance of all skin samples is confirmed to be >20 kΩ as determined by the Transcutaneous Electrical resistance (TER) measurement which is done at 100 Hz.

Example 5: Effect of Topical Capecitabine Formulations in Mouse AK Model

The efficacy of the topical Capecitabine formulations for the treatment of AK is evaluated in a mouse model. Mice treated with a UV-B protocol are recognized as the most relevant models since they develop AK-like lesions and SCCs resembling those seen in humans, although differences exist, such as the thickness of the skin, which is much thinner in mice than in humans. A recent study demonstrated that this mouse model of UV-B-induced skin lesions is predictive for the identification of novel therapeutic treatments for both early and advanced stages of the disease (Pillon et al, 2017).

Such model is the Hairless SKH-1 mice exposed to UV-B. These mice do not develop fur but contrary to nude mice are still immuno-competent. The SKH-1 mice (6-8 weeks old, weighing 18-20 g) in individual housing (one mouse/cage) are exposed to UV-B every day for 14-15 weeks. Medium wave UV-B lamps covering from 280 to 320 nm with an energy peak at 312 nm are used, and 10-12 min of UV-B exposure per day is necessary to reach the MED (minimal erythemal dose) in SKH-1 mice. To generate AK lesions and to prevent the risk of skin burn, gradual exposure is performed during the first 20 days until the MED is reached and maintained for additional 50 to 80 days.

After the UV-exposure period, mice developing actinic keratoses are randomized into treatment groups, each consisting of mice with observable skin lesions of comparable number and size. Treated areas are defined and tattooed to be easily identified. Mice are then treated topically with the Capecitabine topical formulation of the invention, vehicle control and FU cream (Efudx™). All treatments and photographing are performed under isoflurane (1.5%) mixed with air/oxygen (80/20) gas anaesthesia.

Histological and immunohistochemical analysis including p53, Ki67 and CD3 expression detection are preformed along with monitoring the mouse skin for lesion cure to evaluate treatment efficacy.

Example 6: Effect of Capecitabine Formulations in Mouse BCC Model

All BCCs have activation of hedeghog signaling pathway as their pivotal molecular abnormality. Approximately 90% of sporadic BCCs have loss-of-function mutations in PATCHED 1 (PTCH1), and others have activating mutations in the downstream SMOOTHENED (SMO) gene. Based on this knowledge, several murine models have been developed in which the transgenic overexpression of activators or the deletion of repressors drives skin HH signaling.

One of these models is the Ptch1 heterozygous (Ptch1+/−) mice in which p53 is deleted specifically from keratin 14 (K14)-expressing keratinocytes (Ptch1+/−K14-Cre-ER p53 fl/fl). The mice are exposed to ionizing (IR) or UV radiation which produces multiple BCC-like tumors in these mice. Grossly visible tumors are first apparent in irradiated skin after 4 months of UV exposure in Ptch1+/− mice, and by 11 months of UV exposure more than 80% of the mice developpe visible cutaneous tumors (Aszterbaum et al, 1999). The mice are randomized into 3 groups and treated with the topical Capecitabine formulation, topical FU cream (Efudex™) and vehicle control.

Histological and immunohistochemical analysis including Ki67 analysis and hematoxylin and eosin (H&E) staining to measure BCC size are preformed along with monitoring the mouse skin to evaluate treatment efficacy.

It will be appreciated by those skilled in the art that changes could be made to the exemplary embodiments shown and described above without departing from the broad inventive concept thereof. It is understood, therefore, that the disclosure herein is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one."

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

The invention claimed is:

1. A method of treating a subject having a hyperproliferative skin condition or inflammatory skin condition, the method consisting of topically administering a pharmaceutical composition comprising an effective amount of a fluorouracil prodrug therapeutic agent selected from Capecitabine, 5'-deoxy-5-fluorocytidine (5'DFCR), 5'-deoxy-5-fluorouridine (5'DFUR), or combinations thereof to the affected area of the skin of the subject, and optionally topically administering at least one additional pharmaceutical agent other than the fluorouracil prodrug, thereby treating the condition.

2. The method of claim 1, wherein the topical administration of the pharmaceutical composition comprising an effective amount of the therapeutic agent forms a therapeutically effective amount of fluorouracil (FU) within the skin of the subject to treat the hyperproliferative or inflammatory skin condition.

3. The method of claim 1, wherein the therapeutic agent is Capecitabine.

4. The method of claim 1, wherein the therapeutic agent is 5'-deoxy-5-fluorocytidine (5'DFCR).

5. The method of claim 1, wherein the therapeutic agent is 5'-deoxy-5-fluorouridine (5'DFUR).

6. The method of claim 1, wherein the hyperproliferative skin condition is a pre-cancerous or cancerous skin condition selected from the group consisting of actinic keratosis, basal cell carcinoma, squamous cell carcinoma and melanoma.

7. The method of claim 6, wherein the effective amount of therapeutic agent in the composition is from about 0.1% to about 15% by weight of the composition.

8. The method of claim 1, the method includes topically administering at least one additional pharmaceutical agent useful for treating a hyperproliferative or inflammatory skin condition.

9. The method according to claim 8, wherein the at least one additional pharmaceutical agent is selected from the group consisting of diclofenac, imiquimod, ingenol mebutate or other ingenol derivatives, uracil, 5-chloro-2,4-dihydroxypyridine (CDHP), eniluracil, photosensitizing agents, retinoids, interferons, α-hydroxy acids, and caustic agents.

10. A method of providing fluorouracil (FU) to a subject in need thereof, the method consisting of topically administering a pharmaceutical composition comprising an effective amount of a FU prodrug therapeutic agent selected from Capecitabine, 5'-deoxy-5-fluorocytidine (5'DFCR), 5'-deoxy-5-fluorouridine (5'DFUR), or combinations thereof to the skin of the subject, whereby the therapeutic agent is converted to FU in the skin; and optionally topically administering at least one additional pharmaceutical agent other than the FU prodrug.

11. A method of reducing adverse effects of fluorouracil (FU) to a subject with a hyperproliferative skin condition or inflammatory skin condition, the method consisting of topically administering a pharmaceutical composition comprising an effective amount of a FU prodrug therapeutic agent selected from Capecitabine, 5'-deoxy-5-fluorocytidine (5'DFCR), 5'-deoxy-5-fluorouridine (5'DFUR), or combinations thereof to the skin of the subject, whereby the therapeutic agent is converted to FU in hyperproliferating skin or inflammatory cells at a greater rate than non-hyperproliferating or inflammatory skin cells, thereby reducing adverse effects; and optionally topically administering at least one additional pharmaceutical agent other than the FU prodrug.

12. A method of decreasing adverse effects during administration of fluorouracil (FU), the method consisting of topically administering a pharmaceutical composition comprising an effective amount of a FU prodrug therapeutic agent selected from Capecitabine, 5'-deoxy-5-fluorocytidine (5'DFCR), 5'-deoxy-5-fluorouridine (5'DFUR), or combinations thereof to the skin of a subject in need thereof whereby the therapeutic agent is converted to FU in the skin after administration, whereby adverse effects are decreased by a reduction of direct exposure to FU during administration; and optionally topically administering at least one additional pharmaceutical agent other than the FU prodrug.

13. A method of reducing unintended direct exposure to fluorouracil (FU) during administration of FU to a subject in need thereof, the method consisting of topically administering a pharmaceutical composition comprising an effective amount of a FU prodrug therapeutic agent selected from Capecitabine, 5'-deoxy-5-fluorocytidine (5'DFCR), 5'-deoxy-5-fluorouridine (5'DFUR), or combinations thereof to the skin of the subject, whereby the therapeutic agent is converted to FU in the skin, and unintended direct exposure does not occur during the administration process; and optionally topically administering at least one additional pharmaceutical agent other than the FU prodrug.

\* \* \* \* \*

UNITED STATES PATENT AND TRADEMARK OFFICE
CERTIFICATE OF CORRECTION

| | | |
|---|---|---|
| PATENT NO. | : 11,559,541 B2 | Page 1 of 1 |
| APPLICATION NO. | : 16/961214 | |
| DATED | : January 24, 2023 | |
| INVENTOR(S) | : Avramoff et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 84 days.

Signed and Sealed this
Fourteenth Day of January, 2025

Derrick Brent
*Acting Director of the United States Patent and Trademark Office*